United States Patent [19]

Sakariassen et al.

[11] Patent Number: 5,962,418
[45] Date of Patent: Oct. 5, 1999

[54] FACTOR VII-DERIVED PEPTIDES

[75] Inventors: Kjell Steinar Sakariassen, Oslo, Norway; Ross Wentworth Stephens, Copenhagen, Denmark; Lars Orning, Oslo, Norway

[73] Assignee: Nycomed Imaging A/S, Oslo, Norway

[21] Appl. No.: 08/564,063

[22] PCT Filed: Jun. 17, 1994

[86] PCT No.: PCT/GB94/01315

§ 371 Date: May 28, 1996

§ 102(e) Date: May 28, 1996

[87] PCT Pub. No.: WO95/00541

PCT Pub. Date: Jan. 5, 1995

[30] Foreign Application Priority Data

Jun. 18, 1993 [GB] United Kingdom .................... 9312601
May 10, 1994 [GB] United Kingdom .................... 9409335

[51] Int. Cl.$^6$ ................ C07K 7/06; C07K 7/08; A61K 37/02
[52] U.S. Cl. .................. 514/13; 514/2; 514/11; 514/14; 514/15; 514/17; 530/330; 530/325; 530/326; 530/327; 530/328; 530/329; 530/317
[58] Field of Search .................. 514/13, 14, 17, 514/15, 2, 11; 530/330, 325, 326, 327, 328, 329, 317

[56] References Cited

U.S. PATENT DOCUMENTS

| | | | |
|---|---|---|---|
| 4,772,587 | 9/1988 | Tanaka et al. .......................... | 514/19 |
| 5,087,564 | 2/1992 | Mai et al. ............................... | 435/69.7 |
| 5,206,221 | 4/1993 | Lipsky et al. ........................... | 514/19 |
| 5,288,629 | 2/1994 | Berkner ................................. | 435/240.2 |
| 5,298,491 | 3/1994 | Chauveau et al. ...................... | 514/17 |
| 5,496,927 | 3/1996 | Kolb et al. ............................. | 530/328 |

FOREIGN PATENT DOCUMENTS

| | | |
|---|---|---|
| 446797 | 8/1991 | European Pat. Off. . |
| WO 90/03390 | 5/1990 | WIPO . |

OTHER PUBLICATIONS

Rudinger, J 'Characteristics of amino acids as components of peptide hormones sequence' in Peptide Hormones, (ed. J.A. Parsons). University Park Press, Baltimore, pp. 1–7, 1976.

*Primary Examiner*—Cecilia J. Tsang
*Assistant Examiner*—Anish Gupta
*Attorney, Agent, or Firm*—Testa, Hurwitz & Thibeault LLP

[57] ABSTRACT

The present invention relates to compounds comprising the amino acid sequences of the formulae (IA): -CVNENGGCEQYCSD-, (IB): -FCLPAFEGRNCE- and/or (IC): -RCHEGYSLLADGVSCT- as well as peptide fragments thereof, esters, amides, salts and cyclic derivatives thereof, functional analogues thereof and extended peptide chains carrying amino acids or peptides at the termini of the above sequences or fragments, for use in the prevention or inhibition of binding of tissue factor to FVII.

15 Claims, 8 Drawing Sheets

TIME 0

TIME t

HT-1080 CELLS ADHERENT ON
A CYTODEX-3 MICROCARRIER

FACTOR VII-DERIVED PEPTIDES

The present invention is concerned with peptide reagents and compositions thereof which reduce blood clot formation.

Blood clotting relies upon a series or cascade of activating reactions to produce the ultimate fibrin clot. The cascade leading to fibrin formation may be triggered initially in two different ways—by contact with abnormal surfaces (the "intrinsic pathway") or by traumatization of blood vessels which causes secretion of the lipoprotein known as "tissue factor" or TF (the "extrinsic pathway"). The present invention is primarily concerned with the extrinsic blood clotting pathway.

TF is an integral membrane protein which appears on many cell types. However, cells which constitutively express TF, for example the muscle cells of vessels intima, are not normally exposed to blood (see Edgington et al., Thromb. Haemostas. 66(1): 67–69 (1991)). Thus initiation of the extrinsic blood clotting pathway appears to require either the disruption of blood vessel walls (see Almus et al., Blood 76: 354–360 (1990)) and/or activation of endothelial cells or monocytes to express TF (see Edwards et al., Blood ii: 359–370 (1979) and Bevilaqua et al., PNAS USA Da: 4533–4537 (1986)). Disruption of the blood vessel wall may occur due to fissuring of an atherosclerotic plaque which exposes tissue macrophages and smooth muscle cells to the blood (see Wilcox et al., PNAS USA 86: 2839–2843 (1989)). TF may also be exposed following injury to blood vessels during thrombolytic therapy, surgery for grafting, mechanical restoration of vessel patency or other similar techniques. On the other hand, TF expression in endothelial cells or in monocytes may be induced during sepsis due to production of tumour necrosis factor-α or interleukin-1 (see Edwards et al., supra and Gregory et al., J. Clin. Invest. 76: 2440–2445 (1985)).

The serine protease Factor VIIa (FVIIa) is involved in the extrinsic blood clotting pathway. FVIIa is formed by proteolysis from its inactive pro-enzyme Factor VII (FVII) by other participants in the blood clotting process, including Factor Xa, Factor XIIa, Factor IXa or thrombin. Activation of FVII to FVIIa has been reported to be markedly enhanced when FVII is bound to its co-factor tissue factor (TF) (see Nemerson, Semin. Hematol. 29(3): 170–176 (1992)). Yamamoto et al. have also suggested that conversion of FVII to FVIIa may be autocatalytic (see J. Biol. Chem. 267(27): 19089–19094 (1992)).

FVIIa forms a complex with TF in the presence of calcium ions and the FVIIa/TF complex catalyses the conversion of Factor X to its active form, Factor Xa, in the next step of the blood clotting process via the extrinsic pathway.

The structure of FVII has been investigated and the cDNA sequence was reported by Hagen et al. in PNAS USA 83: 2412–2416 (1986). FVII is a vitamin K dependent protein and, by analogy to other vitamin K dependent proteins, a putative γ-carboxyglutamic acid (Gla) domain has been identified at the amino terminal. It was predicted, again by analogy to the other vitamin K proteins, that the Gla domain was required for binding to TF (see Hagen et al., supra). The Gla domain is followed by two potential growth factor (GF) domains. However, the literature has not suggested any function for the GF domains.

Activation of the extrinsic pathway for blood clot formation has been suggested as the primary event leading to fibrin formation (see Weiss et al., Blood 71: 629–635 (1988) and Weiss et al., Blood 73: 968–975 (1989)) and is thus of prime importance in the pathogenesis of arteriosclerotic lesions and in reocculusion and and restenosis following endarterectomy. However effective therapeutic agents able to intervene in the activation of this pathway are not available, despite demand (see Shepard, TIBTECH 9: 80–85 (1991)).

The present invention provides peptides and analogues or salts thereof which inhibit the association of FVII or FVIIa with TF. Through the action of the peptides according to the invention, formation of the FVIIa/TF complex is limited and therefore activation of Factor X is reduced.

Certain peptides stated to be useful in blood clotting therapy are disclosed in WO-A-91/07432 of the Board of Regents, The University of Texas System. The peptides disclosed either occur in the region between the Gla and the first GF domains or in the catalytic domain of FVII or FVIIa. Although inhibition of FVIIa/TF complex formation is discussed, those peptides disclosed in WO-A-91/07432 which cause such an effect do so via inhibition of the Gla function. Such peptides are thus unspecific in their action since other physiological proteins have Gla domains, for example protein C which has close sequence homology to the Gla domain of FVII. Hence, the function of protein C would also be disturbed by peptides disclosed in WO-A-91/07432 in an undesirable way.

In WO-A-90/03390, Corvas Inc. suggest that certain peptides derived from the amino acid sequence of FVII (or FVIIa) might be useful in preventing the action of the fully formed FVIIa/TF complex. Two particular peptide sequences were disclosed in WO-A-90/03390 as being active in this respect. The sequence -VGHFGV- (SEQ ID NO:1) is based upon amino acids nos. 372–377 of FVII which are situated near the carboxy terminus. The other sequence is -SDHTGTKRSCR- (SEQ ID NO:2) which is located at amino acids nos. 103–113 of FVII and is part of the second GF domain. Corvas Inc indicate that these peptides, and analogues thereof, inhibit the cascade reaction initiated by the FVIIa/TF complex.

Furthermore, in Table 1, on page 14 of WO90/03390, it is indicated that of the various regions of the second GF domain, only SDHTGTKRSC (SEQ ID NO:3) (103 to 112) was active and that the other regions, namely from amino acids 50 to 101 and 114 to 127, were totally inactive in inhibition of activation of Factor X by Factor VII and tissue factor.

However, we have shown that, contrary to the reported findings of Corvas Inc., the region SDHTGTKRSC (SEQ ID NO:3) from 103 to 112 is a rather poor inhibitor of the binding of Factor VII to tissue factor and that certain of the regions said to be inactive are, in fact, highly active.

Our initial finding was that a point mutation in FVII, wherein the amino acid glutamine at position 100 was replaced by arginine, was observed in 16 FVII deficient Norwegian patients and suggested that this region of the FVII molecule is important for FVII activity. We established firstly that the amino acid sequence 91–102 was particularly active and that this could usefully also include amino acids 103 and 104. We then found that the amino acid sequence 114–127, also in the GF domain, was relatively active while the Corvas sequence 103–112 had only moderate activity.

Subsequently, we found that the amino acid sequence 72–81 acted synergistically in enhancing the inhibitory action of the peptides of the sequence 91 to 104, and primary utility of peptides derived from the region 72–81 is in such synergistic combinations.

Furthermore, fragments of the above sequences have been found to be inhibitory and in general fragments of 5 or more amino acids from the above sequences will be useful in the inhibition of FVII activity.

The present invention thus concerns peptides comprising the amino acid sequences of formulae

```
-CVNENGGCEQYCSD-    (SEQ ID NO:4)    IA

-FCLPAFEGRNCE-      (SEQ ID NO:5)    IB and/or

-RCHEGYSLLADGVSCT-  (SEQ ID NO:6)    IC
``` as well as peptide fragments thereof, especially fragments having 5 or more amino acids, esters, amides salts and cyclic derivatives thereof, functional analogues thereof and extended peptide chains carrying amino acids or peptides at the termini of the above sequences or fragments.

According to one feature of the invention we provide peptides of the sequences IA, IB and/or IC as defined above, with the exclusion of the peptides

```
CVNENGGCEQYC        (SEQ ID NO:7)    IIA

CLPAFEGRNC          (SEQ ID NO:8)    IIB and

CHEGYSLLADGVSC      (SEQ ID NO:9)    IIC
```

Where appropriate, compounds of formula IA, IB and IC and their various derivatives and fragments are termed, for convenience, peptide IA compounds, peptide IB compounds and peptide IC compounds.

Fragments of the peptide sequences of formulae IA, IB and/or IC include, in particular

```
-VNENG- (SEQ ID NO:10)  -NGGCEQYCSD- (SEQ ID NO:11)

-ENGGC- (SEQ ID NO:12)  -GGCEQYCSD-  (SEQ ID NO:13)

-GGCEQ- (SEQ ID NO:14)

-CEQYV- (SEQ ID NO:15)
```

Our studies have shown that amino acid 95 is important in the peptides of the amino acid sequence 91 to 104 and the peptide of sequence 95 to 104 is the most active inhibitor so far tested. This is NGGCEQYCSD (SEQ ID NO:11).

The peptides of formulae IIA, IIB and IIC are excluded on the basis that they were disclosed in WO90/03390 of Corvas Inc., although stated to have zero inhibitory acticity. There is clearly no suggestion in WO90/03390 that there would be any benefit in making any of the related peptides, including fragments or extensions thereof, for use in combatting blood clotting disorders.

On the basis that WO90/03390 incorrectly reported zero inhibitory activity for the peptides of formulae IIA and IIB one aspect of the present invention provides the therapeutic or diagnostic use of the compounds of formulae IA and/or IB as defined above to bind to tissue factor and thus prevent or inhibit binding of tissue factor to FVII. In the case of peptide IC compounds, these will only be used together with peptide IA or IB compounds. For the sake of clarity, it is emphasised that compounds of formulae IIA, IIB and IIC are included in such use.

According to a further feature of the invention we provide the peptides of formulae IA and/or IB as defined above optionally in combination with peptides of formula IC as defined above.

According to a still further aspect of the invention we provide the use of the compounds of formulae IA and/or IB as defined above, optionally together with peptides of formula IC, for the preparation of pharmaceutical compositions for prevention or inhibition of binding of tissue factor to FVII.

As indicated above, the peptides of the sequence of formula IA are the most active but their activity can be enhanced synergistically by use together with peptides of formulae IB and/or IC and fragments and other derivatives thereof. In such combined use, the peptides may be simply mixed together or they may be covalently linked, for example via disulphide bonds between cysteine residues, or by spacer peptides.

Esters of the peptides of the invention include $C_{1-6}$ alkyl esters and readily cleaved ester groups such as those listed hereinafter as protected carboxyl groups.

Amino acids or peptides attached to the termini of the peptides of the invention may carry functional groups such as protecting groups.

Salts of the peptides of the invention include physiologically acceptable salts such as acid addition salts such as hydrochlorides.

In the sequences referred to above, the standard one letter code is used to refer to each naturally occuring amino acid. This code is standard nomenclature within the art and can be found in any standard biochemical textbook such as "Biochemistry" Stryer, published by W.H. Freeman and Company.

Functional analogues of such peptides are included within the scope of the present invention. It is well known within the art that certain amino acids are functionally equivalent and it has frequently been observed that exchange of such equivalent peptides causes no diminution in protein function. Moreover, substitution of certain non-crucial amino acids may also be made without any, or any significant, loss of function—even where those amino acids have been replaced by chemically dissimilar amino acids. Further, chemical variants of the naturally occurring amino acids are known and substitution by such molecules is also covered by the term "analogue" as used herein.

In the sequence of formula I mentioned above any "C" representing the amino acid cysteine may be replaced by alanine (denoted by "A"). Thus, peptides which are of particular interest include -ENGGA- (SEQ ID NO:16), -GGAEQ- (SEQ ID NO:17) and -AEQYV- (SEQ ID NO:19).

Additionally, peptides derived from the sequence of formula IA, IB and/or IC include chimeric derivatives wherein two normally non-adjacent portions (containing two or more amino acids) of the formula I sequence are juxtaposed. An example of such a chimeric sequence is -EQYVNE- (SEQ ID NO:19).

Optionally the peptides according to the invention may be cyclic, provided the sequence binding to TF is conformationally available for binding. Cyclisation may be achieved by any suitable chemical means including, for example, formation of disulphide bridges between two cysteine amino acids. One example of a cyclic peptide derived from formula I is CVNENGGCEQYC (SEQ ID NO:7).

```
CVNENGGCEQYC               (SEQ ID NO:7).
|_____|
```

The present invention also provides a pharmaceutical composition comprising one or more peptides or analogues or salts thereof, the amino acid sequence of said peptide comprising or being derived from the sequence of formula IA, IB and/or IC above. The peptides may be administered together with any physiologically acceptable excipient known to those skilled in the art, Examples of suitable excipients include water and oil.

The compositions according to the invention may be presented, for example, in a form suitable for oral, nasal, parenteral or rectal administration.

As used herein, the term "pharmaceutical" includes veterinary applications of the invention.

The compounds according to the invention may be presented in the conventional pharmacological forms of administration, such as tablets, coated tablets, nasal sprays, solutions, emulsions, powders, capsules or sustained release forms. Conventional pharmaceutical excipients as well as the usual methods of production may be employed for the preparation of these forms. Tablets may be produced, for example, by mixing the active ingredient or ingredients with known excipients, such as for example with diluents, such as calcium carbonate, calcium phosphate or lactose, disintegrants such as corn starch or alginic acid, binders such as starch or gelatin, lubricants such as magnesium stearate or talcum, and/or agents for obtaining sustained release, such as carboxypolymethylene, carboxymethyl cellulose, cellulose acetate phthalate, or polyvinylacetate.

The tablets may if desired consist of several layers. Coated tablets may be produced by coating cores, obtained in a similar manner to the tablets, with agents commonly used for tablet coatings, for example, polyvinyl pyrrolidone or shellac, gum arabic, talcum, titanium dioxide or sugar. In order to obtain sustained release or to avoid incompatibilities, the core may consist of several layers too. The tablet-coat may also consist of several layers in order to obtain sustained release, in which case the excipients mentioned above for tablets may be used.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Suitable suppositories may, for example, be produced by mixing the active ingredient or active ingredient combinations with the conventional carriers envisaged for this purpose, such as natural fats or polyethyleneglycol or derivatives thereof.

Dosage units containing the compounds of this invention preferably contain 0.1–10 mg, for example 1–5 mg of the peptide of formula (I) or salt thereof.

As indicated above, one aspect of the invention provides peptides (including the analogues or salts thereof) according to the invention for use in the treatment or prevention of blood clotting disorders or problems. Blood clotting disorders include thrombosis (particularly vascular thrombosis or deep vein thrombosis), acute myocardial infarction, restenosis, reclosure, angina, cerebrovascular disease, peripheral arterial occlusive disease, hypercoagulability and pulmonary embolism. The peptides according to the invention can also be used to prevent occurrence of blood clotting problems caused by, for example, injury to blood vessels during thrombolytic therapy, grafting surgery, vessel patency restoration etc. Blood clotting disorders may be triggered by sepsis due to production of TNF-α or IL-1.

In a still further aspect, the present invention also provides a method of treatment of blood disorders in the mammalian, preferably human, animal body, said method comprising administering to said body one or more peptides of formula IA, IB and/or IC as defined above, including compounds of formulae IIA, IIB and/or IIC, or analogues or salts thereof. Prophylactic methods of treatment are also provided, whereby a peptide according to the invention is administered to a patient to prevent or reduce the occurrence of possible blood clotting problems, for example during surgery or other invasive techniques. The peptide will of course normally be administered in the form of a pharmaceutically acceptable composition.

In another aspect, the present invention provides a process for the preparation of peptides which comprise the sequence of formula I or are derived therefrom, or analogues or salts thereof.

The peptides of the invention may be synthesised in any convenient way. Generally the reactive groups present (for example amino, thiol and/or carboxyl) will be protected during overall synthesis. The final step in the synthesis will thus be the deprotection of a protected derivative of the peptide of the invention.

In building up the peptide chains, one can in principle, start either at the C-terminal or the N-terminal although only the C-terminal starting procedure is in common use.

Thus, one can start at the C-terminal by reaction of a suitably protected derivative of, for example lysine with a suitably protected derivative of cysteine or cystine. The lysine derivative will have a free α-amino group while the other reactant will have either a free or activated carboxyl group and a protected amino group. After coupling, the intermediate may be purified, for example by chromatography, and then selectively N-deprotected to permit addition of a further amino acid residue. This procedure is continued until the required amino acid sequence is completed.

Carboxylic acid activating substituents which may, for example, be employed include symmetrical or mixed anhydrides, or activated esters such as for example the p-nitrophenyl ester, 2,4,5-trichlorophenyl ester, N-hydroxybenzotriazole ester (OBt), or N-hydroxysuccinimidyl ester (OSu).

The coupling of free amino and carboxyl groups may, for example, be effected using dicyclohexylcarbodiimide (DCC). Another coupling agent which may, for example, be employed is N-ethoxycarbonyl-2-ethoxy-1,2-dihydroquinoline.

In general it is convenient to effect the coupling reactions at low temperatures, for example, −20° C. up to ambient temperature, conveniently in a suitable solvent system, for example, tetrahydrofuran, dioxan, dimethylformamide, methylene chloride or a mixture of these solvents.

It may be more convenient to carry out the synthesis on a solid phase resin support. Chloromethylated polystyrene (cross-linked with 1% divinyl benzene) is one useful type of support; in this case the synthesis will start at the C-terminal, for example by coupling N-protected lysine to the support.

A number of suitable solid phase techniques are described by Eric Atherton, Christopher J. Logan, and Robert C. Sheppard J. Chem.Soc. Perkin I, 538–46 (1981); James P. Tam, Foe S. Tjoeng, and R. B. Merrifield J. Am. Chem. Soc. 102 6117–27 (1980); James P. Tam, Richard D. Dimarchi and R. B. Merrifield Int. J. Peptide Protein Res 16 412–25 (1980); Manfred Mutter and Dieter Bellof, Helvetica Chimica Acta 67 2009–16 (1984).

A wide choice of protecting groups for amino-acids are known and are exemplified in Schröder, E., and Lübke, K., The Peptides, Vols. 1 and 2, Academic Press, New York and London, 1965 and 1966; Pettit, G. R., Synthetic Peptides, Vols. 1–4, Van Nostrand, Reinhold, New York 1970, 1971, 1975 and 1976; Houben-Weyl, Methoden der Organischen Chemie, Synthese von Peptiden, Band 15, Georg Thieme Verlag, Stuttgart 1974; Amino Acids, Peptides and Proteins, Vol.4–8, The Chemical Society, London 1972, 1974, 1975 and 1976; Peptides, Synthesis-physical data 1–6, Wolfgang Voelter, Eric Schmidt-Siegman, Georg Thieme Verlage Stuttgart, NY, 1983; The Peptides, Analysis, synthesis, biology 1–7, Ed: Erhard Gross, Johannes Meienhofer, Academic Press, NY, San Fransisco, London; Solid phase peptide synthesis 2nd ed., John M. Stewart, Janis D. Young, Pierce Chemical Company.

Thus, for example amine protecting groups which may be employed include protecting groups such as carbobenzoxy (hereinafter also designated Z) t-butoxycarbonyl (hereinafter also designated Boc), 4-methoxy-2,3,6-trimethylbenzene sulphonyl (Mtr) and 9-fluorenylmethoxycarbonyl (hereinafter also designated Fmoc). It will be appreciated that when the peptide is built up from the C-terminal end, an amine-protecting group will be present on the α-amino group of each new residue added and will need to be removed selectively prior to the next coupling step. One particularly useful group for such temporary amine protection is the Fmoc group which can be removed selectively by treatment with piperidine in an organic solvent.

Carboxyl protecting groups which may, for example be employed include readily cleaved ester groups such as benzyl (Bzl), p-nitrobenzyl (ONb), pentachlorophenyl (OPClP), pentafluorophenyl (OPFP) or t-butyl (OtBu) groups as well as the coupling groups on solid supports, for example methyl groups linked to polystyrene.

Thiol protecting groups include p-methoxybenzyl (Mob), trityl (Trt) and acetamidomethyl (Acm).

It will be appreciated that a wide range of other such groups exists as, for example, detailed in the above-mentioned literature references, and the use of all such groups in the hereinbefore described processes fall within the scope of the present invention.

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoro acetic acid. Thiol protecting groups such as Trt may be removed selectively using an oxidation agent such as iodine.

The following Examples are given by way of illustration only.

Figure 1A:
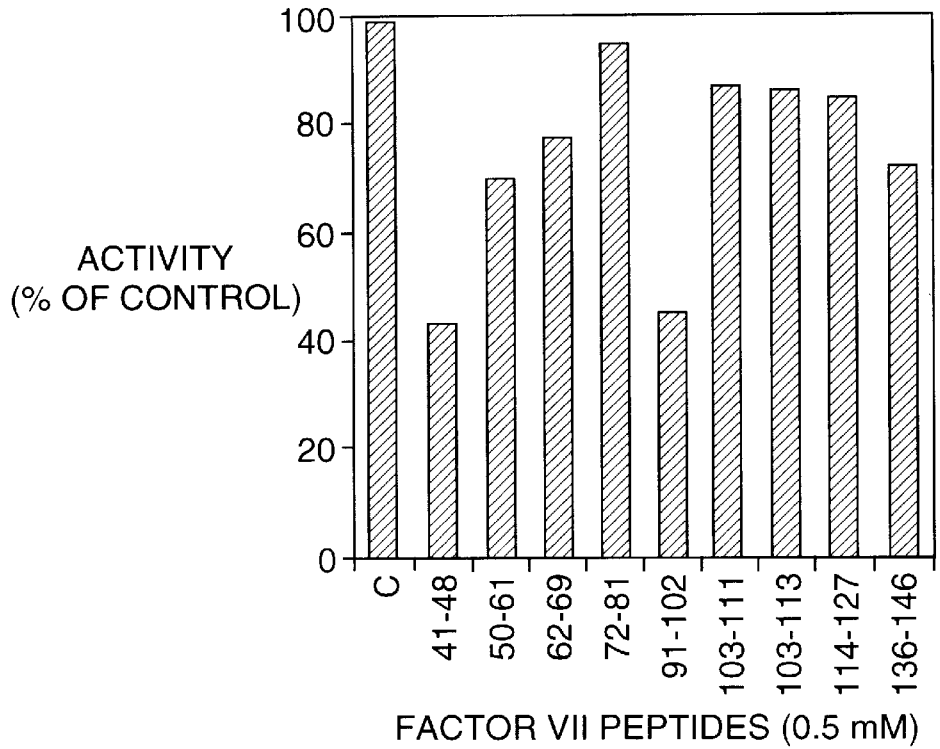
FIGS. 1A–1B illustrates the inhibition of blood clotting by different FVII peptides and FVII peptide analogues.

The present invention is further illustrated by the following, non-limiting, examples.

The following abbreviations are used in the Examples:
TFA: trifluoroacetic acid
BocAA: t-butoxy carbonyl protected Amino acid
BOP: benzotriazol-1-yloxy-tris-(dimethylamino) phosphonium-hexafluorophosphate
HOBT: N-hydroxybenzotriazole
DIEA: diisopropylethylamine
DCM: dichloromethane
NEM: N-ethylmaleimide EDTA: ethylenediaminetetraacetic acid
DMF: dimethylformamide

EXAMPLE 1
General Peptide Synthesis

The peptides used were synthesized by standard procedures of solid phase chemistry and purified by preparative HPLC. The purity of each peptide was checked by analytical HPLC, amino acid analysis and mass spectrometry. All were products of Neosystems Laboratoire (Strasbourg, France).

The peptides were assembled and cleaved using the following general procedure.

The resin used was 4-methylbenzhydrylamine (batch R2161) with an initial loading of 0.9 meq/g. For each peptide 450 mg of starting resin (0.4 mmol) was used.

1. Assembling

After neutralisation, the coupling/deprotection protocol described below was used (volume: 10 ml for each solvent).

| a) Neat TFA | 1 min. |
|---|---|
| b) Neat TFA | 3 min. |
| c) Flow wash methylene chloride | |
| d) Isopropanol | 0.5 min. |
| e) Dimethylformamide (DMF) | 0.5 min (3 times) |
| f) Dimethylformamide flow wash | |

Coupling 5 eq. of BocAA, BOP and HOBT were dissolved in 5 ml of DMF and added to the resin. After bubbling started 0.5 ml of diisopropylethylamine was added and agitation was continued for 13 minutes. After 2 DMF washes a double coupling was performed in the same conditions.

Acetylation

After the last deprotection step, acetylation was performed using 10 eq. of acetic anhydride and 10 eq. of DIEA in 10 ml of DMF.

Reaction time: 10 minutes.

Once assembling was achieved, the peptide resin was washed with DMF, DCM ether and then dried under nitrogen stream.

2. Cleavage

The peptide was cleaved from the resin and deprotected by a treatment with HF/anisole (9/1 by volume. 10 ml per gram of peptide resin) at 0° C. for 45 minutes.

After evaporation of the HF and precipitation with ether, the crude peptide was solubilised in neat TFA and filtered.

The TFA was then evaporated under reduced pressure and the peptide was again precipitated with ether. At this stage the product was ready to be purified.

3. Purification and analysis

Each peptide was HPLC purified on reversed phase C18 column (15–25 μm) using a linear gradient of acetonitrile/water (0.1% TFA). The fractions with a purity >95V were pooled and lyophilised. The purified peptide was then analysed by HPLC and a sample was hydrolized for amino acid analysis. The results were noted on the analytical data sheet which was sent with each peptide.

The basic strategy used for purification was always the same. Only the gradiant used for the preparative purification was different, depending on the initial retention time of each individual peptide.

The peptide resulting from the above procedure carries an acetyl group at the N-terminal and a $CONH_2$ group at the C-terminal.

EXAMPLE 2
PEPTIDE FVII-5

The resin used Boc-Cys(4-MeBzl)-PAM resin (batch 52172) with an initial loading of 0.63 meq/g. 0.96 g of the starting resin (0.6 mmol) was used.

The assembling/coupling/cleavage procedure used was the same as described above, with the following modifications:

1. Assembling

| a) TFA 55% in DCM | 5 min. |
|---|---|
| b) TFA 55% in DCM | 25 min. |

2. Cleavage

After precipitation with ether, the peptide resin was washed with 30 ml 10% acetic acid in water and lyophilised.

The peptide resulting from such cleavage has a C-terminal COOH group and an N-terminal $NH_2$ group.

3. Purification-cyclisation

Solvent composition:
A: water 0.1t TFA
B : acetonitrile/solvent A (60/40 by volume).

The crude product was pre-purified on reversed phase HPLC using a linear gradiant of acetonitrile/water (0.1% TFA), 10 to 80% of B, 30 minutes.

All the fractions containing the linear peptide with a purity >80 were pooled and the volume was adjusted to 0.5 liter with water. The pH of the solution was adjusted to 8.5 with DIEA and left overnight at ambient temperature, under magnetic stirring. The evolution of the cyclisation reaction was followed by co-injection of a sample of the reaction mixture with N-ethylmaleimide (NEM).

After 24 hours, cyclisation was complete. The pH was then decreased to 2.5 with acetic acid and the solution concentrated under reduced pressure before lyophilisation.

The cyclic peptide was then purified up to 95% by RP-HPLC (linear gradiant from 5 to 30% of B in 30 minutes).

Purity and identity of the final product were then controlled by analytical HPLC, amino acid analysis and mass spectrometry.

EXAMPLE 3
PEPTIDE FVII-1

This peptide was synthesised using Fmoc/t-But strategy starting from 90 mg of Fmoc-Ala-Wang resin (0.67 meq/g).

1. Assembling

The following protocol was used for deprotection/coupling:

| a) Piperidine 25% in DMF | 2 min. |
|---|---|
| b) Flow wash DMF | |
| c) Piperidine 25% in DMF | 4 min. |
| d) Flow wash DMF | |
| e) Piperidine 25% in DMF | 6 min. |
| f) Flow wash DMF | repeat 5 times. |

2. Coupling 5 eq. of Fmoc-AA, BOP and HOBT were dissolved in 3 ml of DMF and added to the resin. After bubbling started, 0.13 ml of DIEA was added and coupling was continued for 13 minutes. After 2 DMF washes, a double coupling was performed as described above.

3. Cleavage

Cleavage of the peptide and deprotection were achieved by a treatment with 5 ml of a mixture of TFA (83.3 V), water (4.2%), thioanisole (4.2%), ethandithiol (2.1 A) and phenol (6.25%) for 2.5 hours. After filtration this mixture was poured into 25 ml of cold ether. The precipitated peptide was centrifuged and washed twice with ether. The product was then dissolved in water, lyophilized and used without further purification.

EXAMPLE 4

Other synthetic peptides were produced by analogy to the procedure described in Example 1.

Cyclic compounds were produced by the method of Example 2.

Table 1 lists all the peptides synthesised.

TABLE 1

FACTOR VII PEPTIDES

| DESIGNATION | SEQUENCE | RESIDUES IN FVII |
|---|---|---|
| FVII-12 | LFWISYSD (SEQ ID NO: 20) | 39–46 |
| FVII-21 | WISYSDGD (SEQ ID NO: 21) | 41–48 |
| FVII-23 | SYSDGD (SEQ ID NO: 22) | 43–48 |
| FVII-7(cyclic) | CASSPCQNGGSC (SEQ ID NO: 23) | 50–61 |
| FVII-13 | KDQLQSYI (SEQ ID NO: 24) | 62–69 |
| FVII-8(cyclic) | CLPAFEGRNC (SEQ ID NO: 8) | 72–81 |
| FVII-5(linear) | CVNENGGCEQYC (SEQ ID NO: 7) | 91–102 |
| FVII-5(cyclic) | CVNENGGCEQYC (SEQ ID NO: 7) | 91–102 |
| 5A | VNENG (SEQ ID NO: 10) | 92–96 |
| 5B | ENGGA (SEQ ID NO: 16) | 94–98 |
| 5C | GGAEQ (SEQ ID NO: 17) | 96–100 |
| 5D | AEQYV (SEQ ID NO: 18) | 98–102 |
| 5E | EQYVNE (SEQ ID NO: 19) | 99–101 + 92–94 |
| FVII-4B | SDHTGTKRS (SEQ ID NO: 25) | 103–111 |
| FVII-6(cyclic) | CHEGYSLLADGVSC (SEQ ID NO: 9) | 114–127 |
| FVII-1 | GKIPILEKRNA (SEQ ID NO: 26) | 136–146 |

EXAMPLE 5
Assay of FVIIa/TF Activity

Peptides (0–1 mM) were preincubated in 0.1 M Tris.HCl pH 7.2 with tissue factor (Thromborel®, Behringwerk, Marburg, Germany; 0.2% final concentration) at 22° C. for 30 minutes, then Factor X (American Diagnostica Inc., Greenwich, Conn. USA; 70 nM was added followed by FVIIa (Diagnostica Stago, Asnières, France; 8 pM and CaCl$_2$ (5 mM). Incubations were continued for 30 minutes and quenched with EDTA (50 mM) which removes essential Ca$^{2+}$. The FXa produced was quantified by monitoring hydrolysis of the chromegenic FX substrate S-2222 (Chromogenix, Mölndal, Sweden).

Figure 1B:
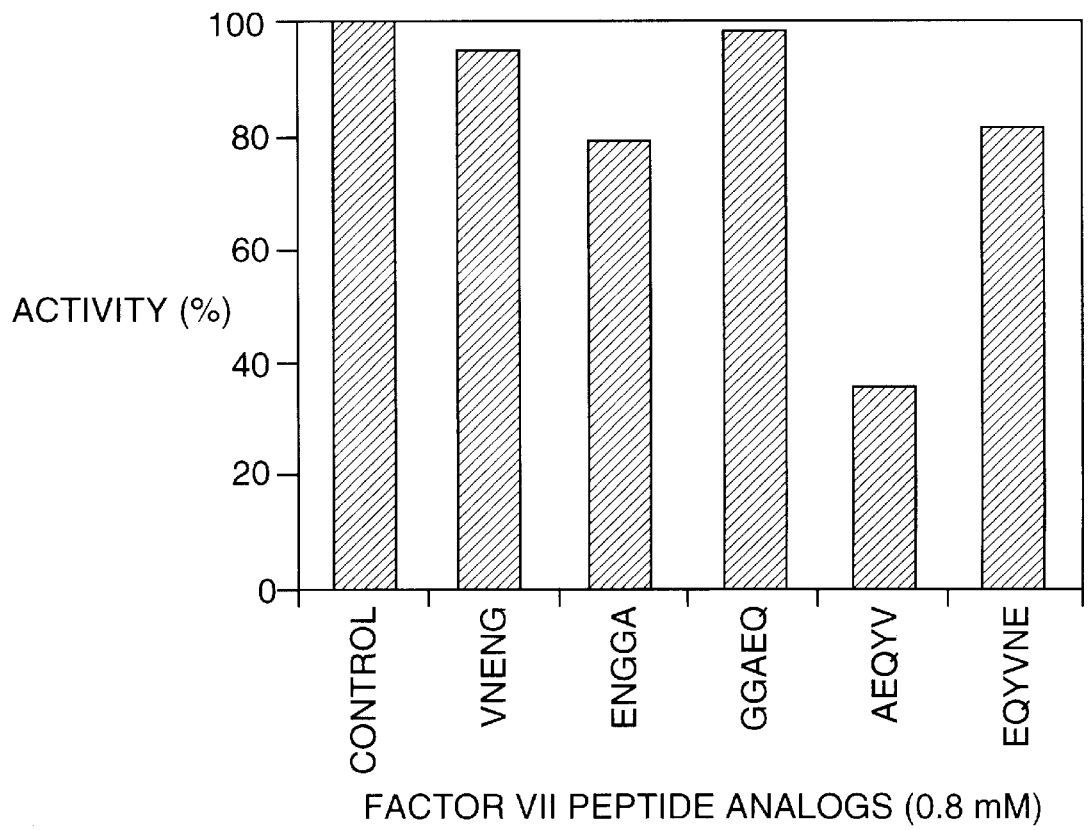

The results are shown in FIGS. 1A–1B.

EXAMPLE 6

The effect of different concentrations of the peptide FVII-5 was investigated using the assay procedure described in Example 5. The experiment was repeated using the peptide FVII-5D.

Figure 2:
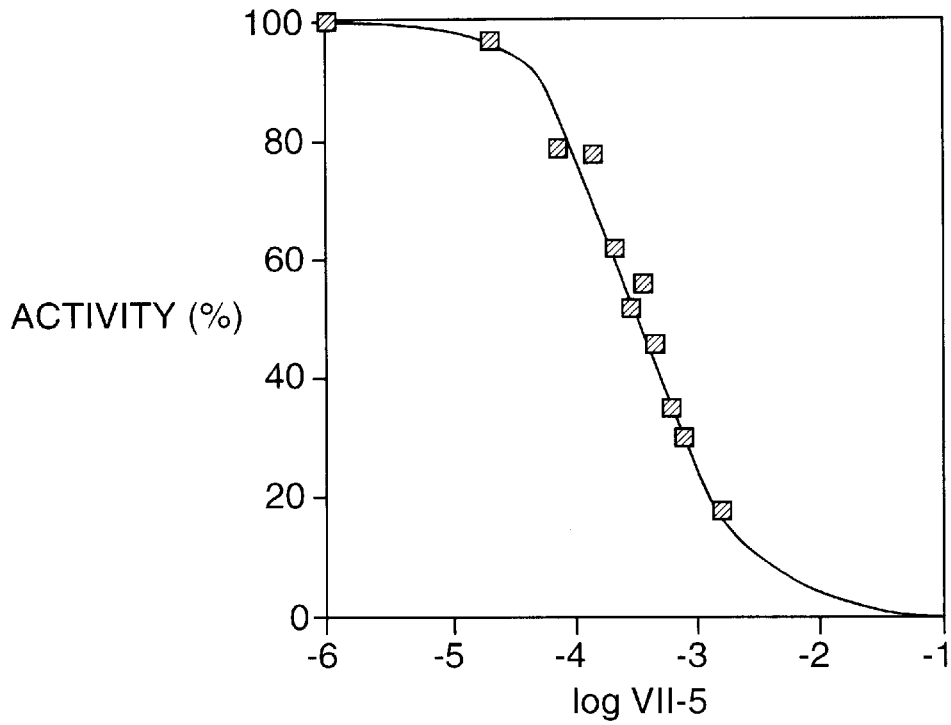
FIG. 2 shows the dose-response relationship between FVII/TF activity and the peptide FVII-5.
Figure 3:
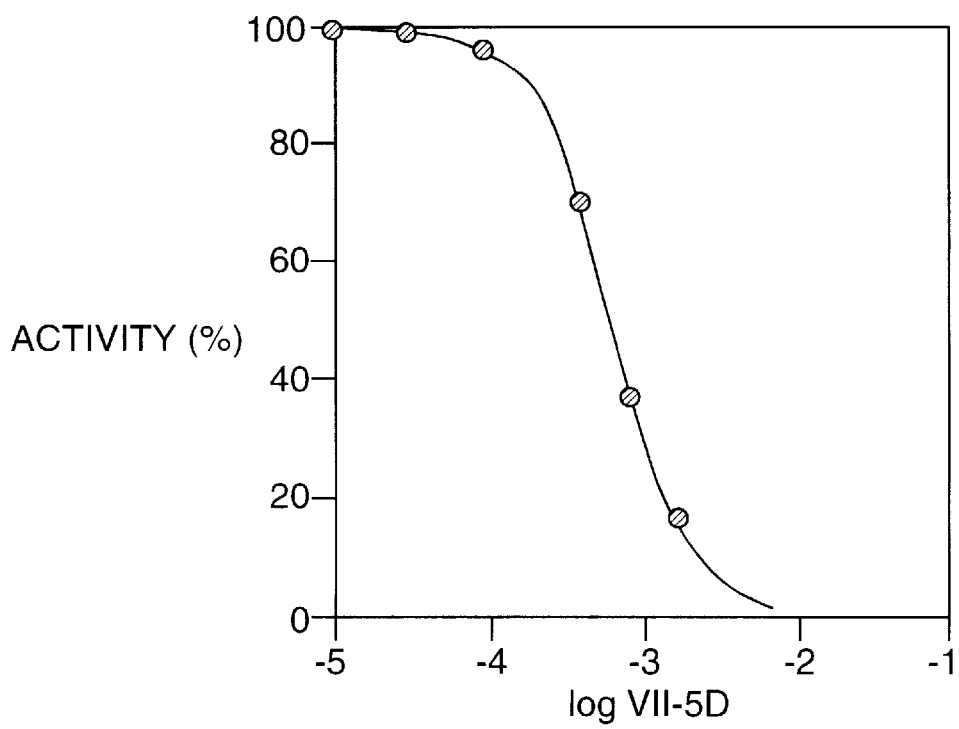
FIG. 3 is the dose-response relationship between FVII/TF activity and the peptide FVII-5d.

The results are shown in FIGS. 2 and 3 respectively.

EXAMPLE 7

The kinetics of inhibition of FX activation by FVII-5 was investigated. Varying concentrations of FVII-5 were incubated with different concentrations of Factor X in the presence or absence of TF and FVIIa.

Figure 4A:
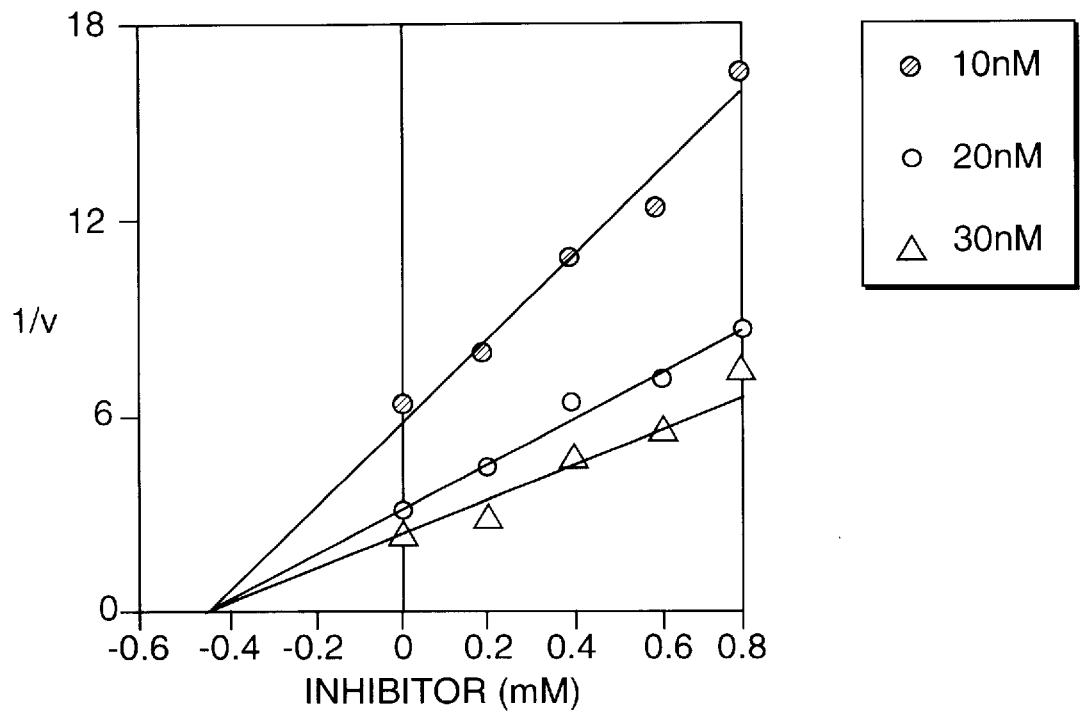
FIGS. 4A–4B shows the inhibition of Factor X activation at different concentrations of FVII-5.
Figure 4B:
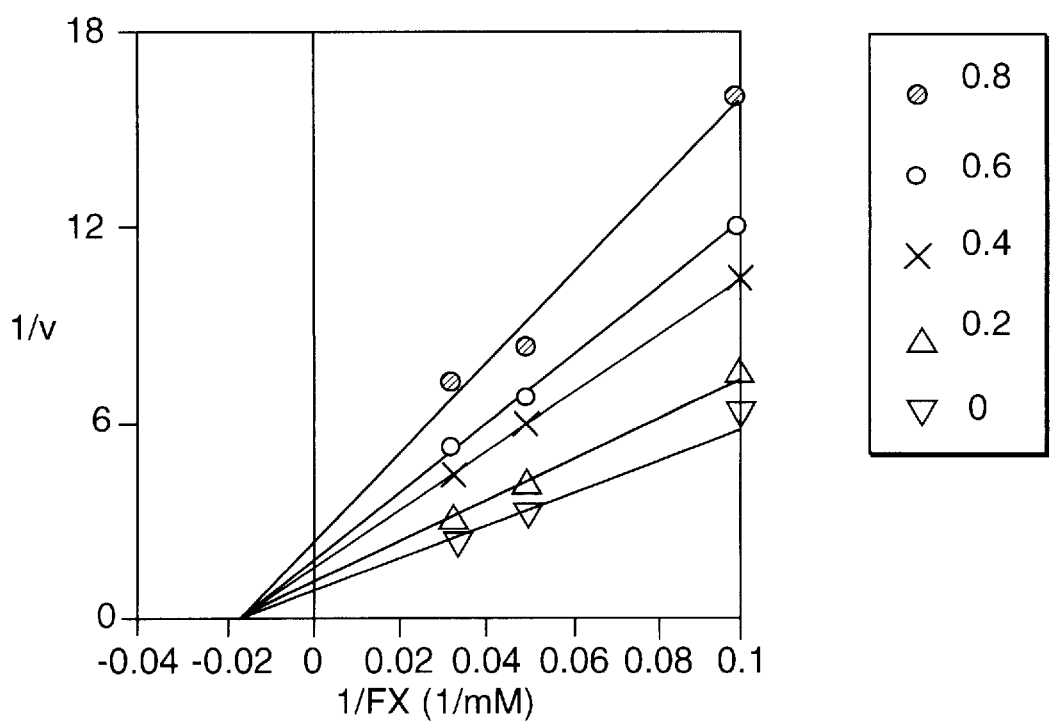

The results are shown in FIGS. 4A–4B. Both graphs are based upon the same data and both indicate a noncompetitive inhibition of Factor X activation by FVII-5 thus indicating that inhibition occurs at an earlier step than Factor X binding ie. inhibition occurs at FVIIa/TF complex formation.

EXAMPLE 8
Assay of apoTF/FVIIa Catalytic Activity

This calorimetric assay was used to measure directly the amidolytic (catalytic) activity of purified human FVIIa when bound to recombinant human TF in the absence of phospholipid.

Protocol

Reactions were performed in microtitre plate wells, using a final incubation volume of 200 uL. Test compounds, dissolved in water, (final concentration, 0–1 mM) were preincubated with recombinant human tissue factor (American Diagnostica, cat# 4500; 5 nM) and CaCl$_2$ (5 mM) in Tris buffer (100 mM), pH 7.2, containing NaCl (150 mM) and BSA (1 mg/mL) at ambient temperature for 30 minutes. Factor Vlla (Enzyme Research Laboratories, cat# HFVlla; 5 nM) was added and the incubations continued for 60 minutes. Chromogenic substrate, S2288 (Chromogenix cat# 820852; 0.5 mM) was then added and the enzymatic activity of the tissue factor apoprotein/factor VII complex (apoTF/FVlla) was monitored at 405 nm.

EXAMPLE 9
Assay of HT1080 Cell Surface TF/FVIIa Mediated Activation of FX

This assay system was used to measure the catalytic activity of native TF/FVIIa complex on the surface of living cells expressing TF in their cell membrane. The activity was measured as the amidolytic (catalytic) activity of FXa produced by the action of the cell surface TF/FVIIa on added FX. The cell line chosen for this assay was the human fibrosarcoma HT-1080 (American Type Culture Collection CCL 121).

Protocol

HT-1080 cells were suspended in a small volume of serum-containing medium and mixed with microcarriers (Cytodex-3, Pharmacia) in a ratio of about 50–100 cells/microcarrier. The cells were usually adherent on the microcarriers within 2 h and could then be transferred to normal roller bottles with a larger volume of culture medium. The microcarrier cell preparations were then washed twice in calcium free buffer to remove bound serum factors. Of nine different washing buffers tested, 'Hank's buffered salt solution' was found to be optimal when considering i) low carry-over of serum factors, ii) small effect on cell adhesion to microcarrier spheres, iii) little damage to cell membranes, and iv) high cell surface TF activity. The microcarrier spheres were resuspended in Hank's buffer and the beads were counted.

FVII (Enzyme Research Laboratories cat# HVII 1007; 5 pM) (and inhibitor in inhibition assays) was then added and the mixure allowed to equilibrate for 30 minutes before addition of FX (Enzyme Research Laboratories cat# HFX 1010; 50 nM) and CaCl$_2$ (5 mM). The rate of FX formation was determined by an amidolytic assay using chromogenic substrate S2765 for FXa (Chromogenix cat# 821413) and measurement of the absorbance increase at 405 nm. The TF activity was easily adjusted by simple dilution of the microcarrier suspension. The variation could be kept at a minimum by stirring the suspension when aliquots were removed. It was determined as 14±7%.

Figure 5:
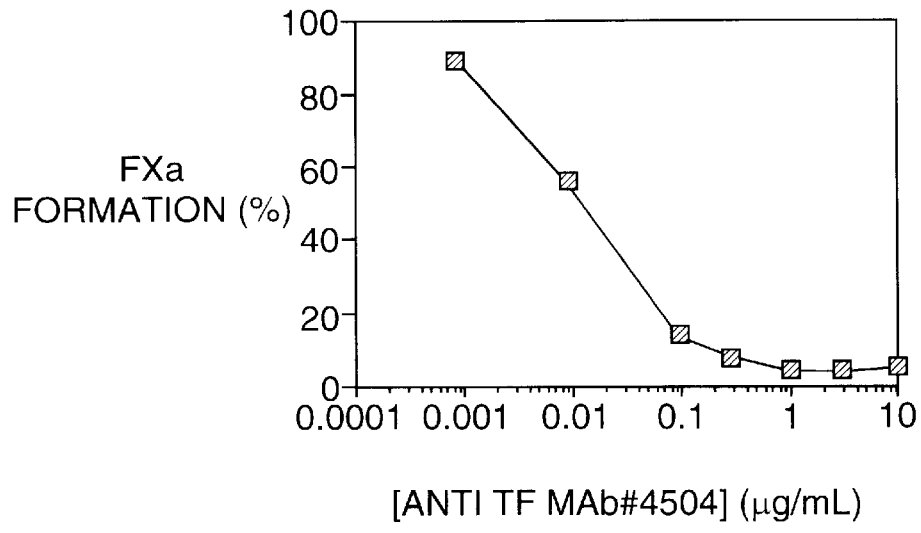
FIG. 5 Inhibition of the cell mediated activation of factor X by a neutralizing monoclonal antibody to tissue factor (American Diagnostica #4504). HT-1080 cells and antibody were preincubated for 1 hour at room temperature before the addition of factor VII (5 pM) and factor X (56 nM). Reactions were continued for 2 hours and quenched by the addition of EDTA. Formation of factor Xa was monitored by an amidolytic assay using a factor Xa chromogenic substrate (Chromogenix S2765). Inhibition reached >95% indicating complete dependence on tissue factor.
Figure 6:
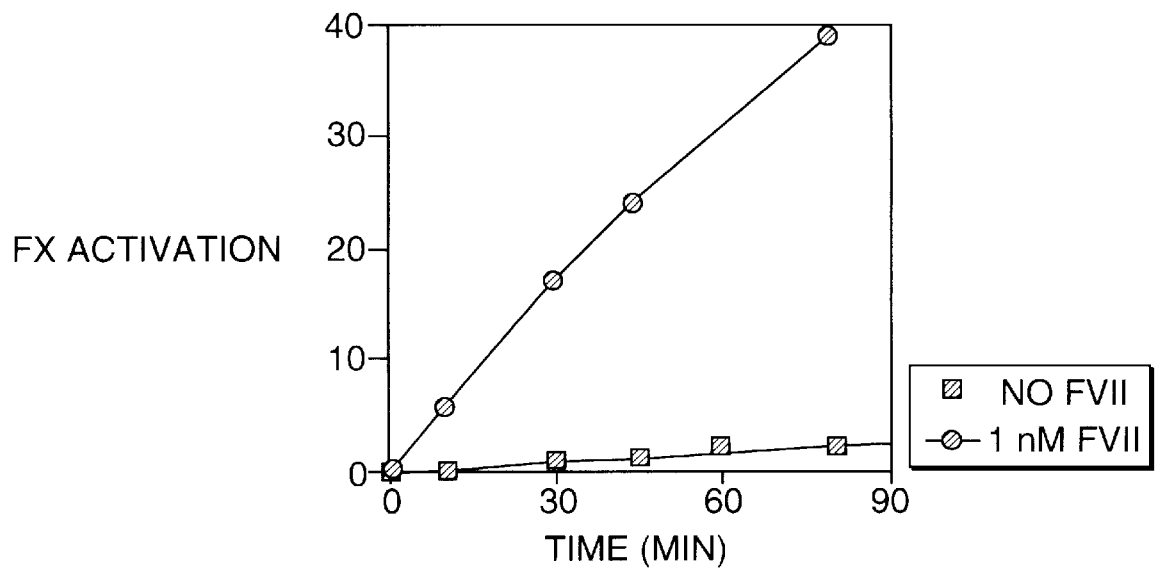
FIG. 6 Time course for factor X activation using 0 (■) and 1 nM (●) factor VII.
Figure 7:
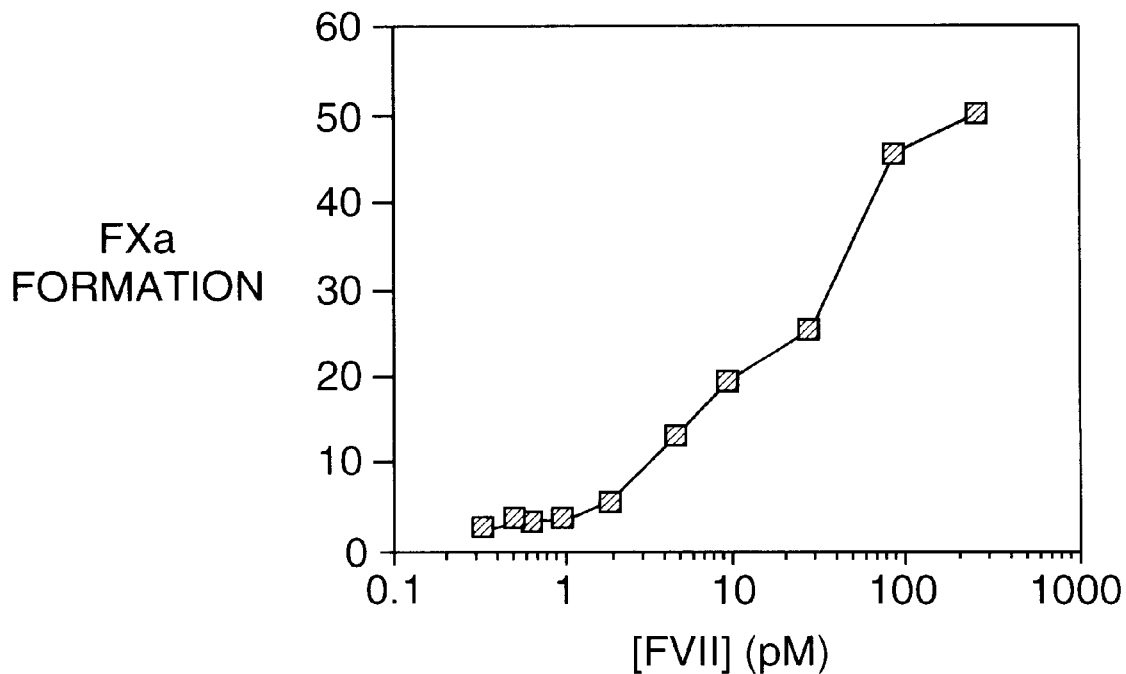
FIG. 7 Dependence of cell mediated factor X activation on added factor VII. Mean of triplicate determinations. Intra-assay variation was 12±14%.
Figure 8:
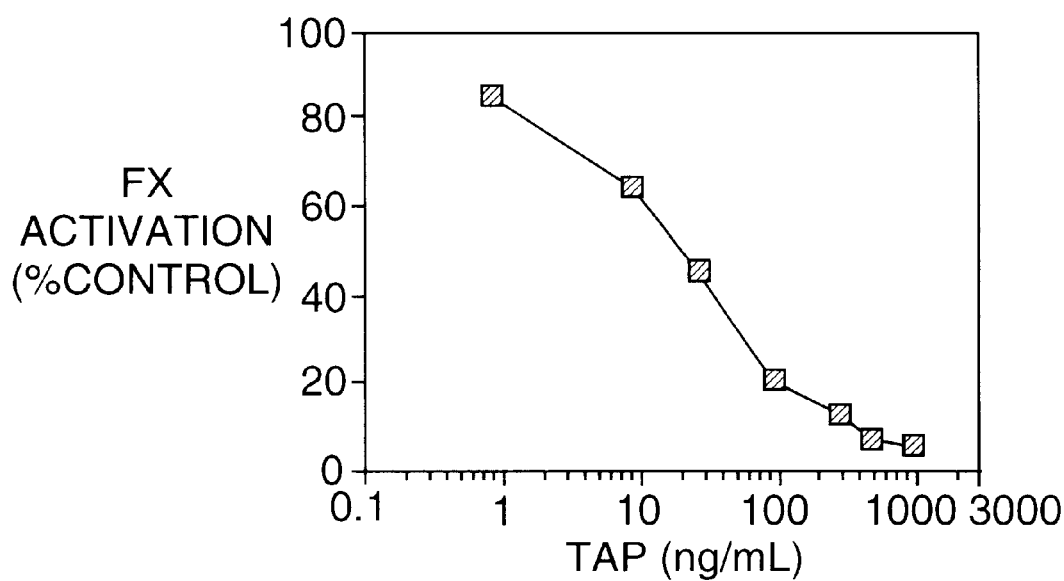
FIG. 8 Inhibition by TAP (tick anticoagulant polypeptide) of Fxa amidolytic activity generated by HT-1080 cell-surface TF/FVIIa.

That FX activation by the cells was truly dependent upon cell-surface TF could be shown by the use of a neutralizing monoclonal antibody to human TF as depicted in FIG. 5. Titration of cell-bound TF with FVII indicated about 11,000 TF molecules per cell or 0.8 ng/10$^6$ cells. Also FX activation was dependent on incubation time and FVII added (FIGS. 6 & 7). That the activity measured represented FXa was verified by inhibition of activity with TAP (tick anticoagulant polypeptide; G. Vlasuk, Corvas Int.) (FIG. 8).

EXAMPLE 10
Assay of Cell-surface TF Initiated Coagulation of Plasma

Figure 9A:
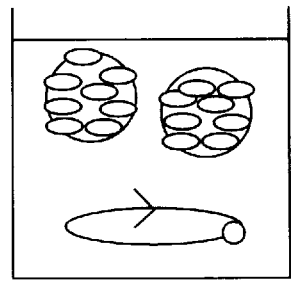
FIGS. 9A–9C Principle of the microcarrier assay of cell-surface mediated coagulation of blood plasma. Living cells (e.g., human HT-1080 fibrosarcoma; ATCC CRL 121) adherent on the surface of microcarriers are mixed with a calcium-containing buffer and plasma in the incubation well of a Thrombotrack™ electromagnetic coagulometer (Nycomed). The clotting time is measured by the increase in resistance to movement of a magnetic ball produced by the formation of fibrin fibres. HT-1080 cells adherent on Cytodex-3 microcarriers are shown in FIG. 9C as an example of the types of cells expressing TF which may be used.
Figure 9B:
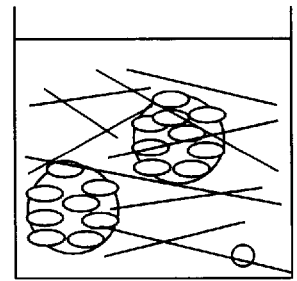
Figure 9C:
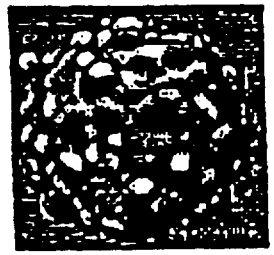
Figure 10:
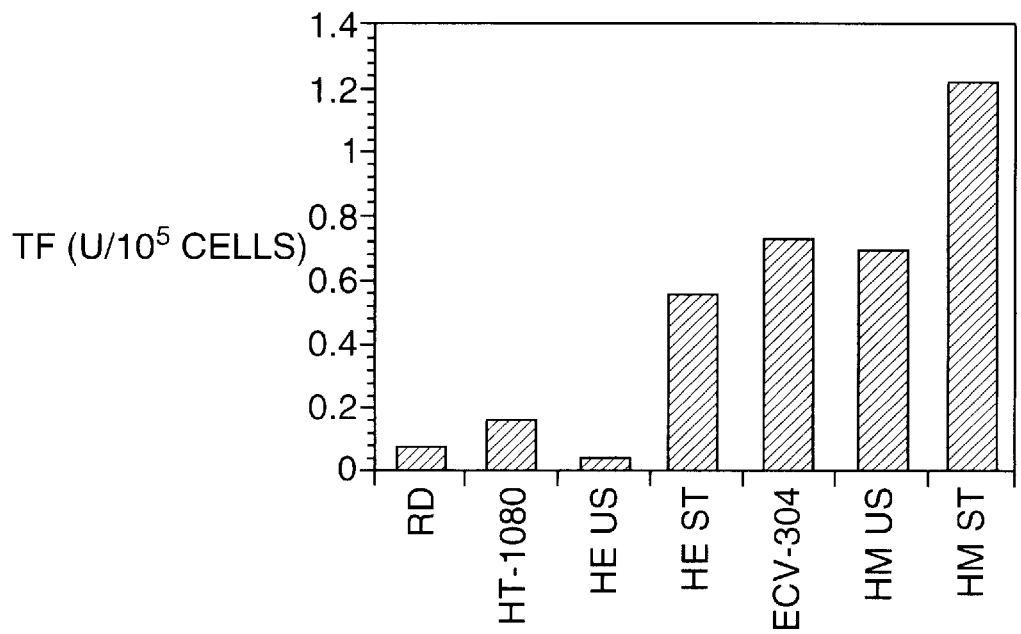
FIG. 10 Coagulant activity of a selection of cell types adherent on microcarriers. The activity is expressed as TF units per $10^5$ cells, calculated from a calibration curve generated with rabbit brain thromboplastin (Nycomed). The cell types shown are: RD, human rhabdomyosarcoma cells (ATCC CCL 136); HT-1080, human fibrosarcoma cells (ATCC CRL 121); HE US, unstimulated primary culture of human umbilical vein endothelial cells; HE ST, human umbilical vein endothelial cells after stimulation with bacterial lipopolysaccharide (1 μg/ml; 5 h); ECV-304, human endothelial cells (ATCC CRL 1998); HM US, unstimulated human peripheral monocytes and HM ST, human peripheral monocytes after stimulation with bacterial lipopolysaccharide (0.5 μg/ml; 2 h).

A novel assay system has been devised to measure the coagulation of blood plasma (i.e. clotting time) induced by tissue factor (TF) expressed on the surface of living cells. This assay makes use of human or animal cells adherent on the surface of microcarriers (see FIG. 9), which enables reproducible presentation of known amounts of TF activity in the stirred measuring well of an electromagnetic coagulometer. The cells used may be normal or transformed, and representing phenotypes such as monocytes, endothelium, fibroblasts etc (see FIG. 10).

This novel assay has been particularly developed and characterised so as to be highly useful in determining the effect of synthetic peptides and peptidomimetic compounds on the extrinsic pathway of coagulation, using living cells in a plasma milieu. Results for the inhibitory effect of synthetic peptides based upon the amino acid sequence of human FVII are disclosed.

Protocol

The microcarrier cell preparation is made as follows. Cells obtained from primary isolates or subcultures of transformed lines (see FIG. 10) are suspended in a small volume of serum-containing medium and mixed with microcarriers (Cytodex-3, Pharmacia) in a ratio of about 50–100 cells/microcarrier. The cells are usually adhere nt on the microcarriers within 2 hours, and can then be transferred to normal roller bottles with a larger volume of culture medium. Uniform coverage of microcarriers with about 20–60 cells can be obtained directly with transformed cells, when large cell numbers are available, or after 2 days growth when primary cultures (e.g. umbilical vein endothelial cells) are used. Primary cultures of cells not expressing TF (e.g. monocytes or endothelial cells) may be stimulated to express TF by incubation of the adherent cells with such agents as bacterial lipopolysaccharide (LPS) or tumour necrosis factor-alpha (TNF-α) (see FIG. 10).

To assay the extrinsic coagulation activity, the microcarrier cell preparations are first washed with a calcium-free buffer to remove bound serum factors. A calcium-containing buffer and plasma are then added and the clotting time is determined automatically in an electromagnetic coagulometer. The clotting time may be very conveniently adjusted (e.g. 35 sec) by simple dilution of the microcarrier suspension, and reproducibility is easily obtained provided the suspension is stirred when aliquots are removed. The clotting time may be converted to arbitrary TF units by a log-log calibration curve generated with rabbit brain thromboplastin.

Figure 11:
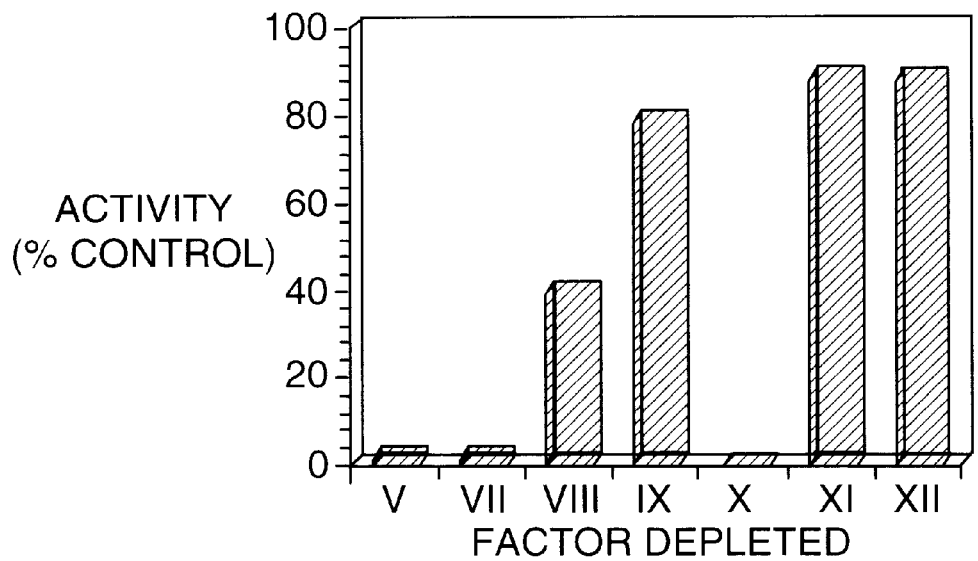
FIG. 11 Dependence of ECV-304 mediated coagulation on specific coagulation factors, demonstrated by the use of immunodepleted human plasmas (American Diagnostica) in the microcarrier assay. Note complete dependence on factors VII and X.
Figure 12:
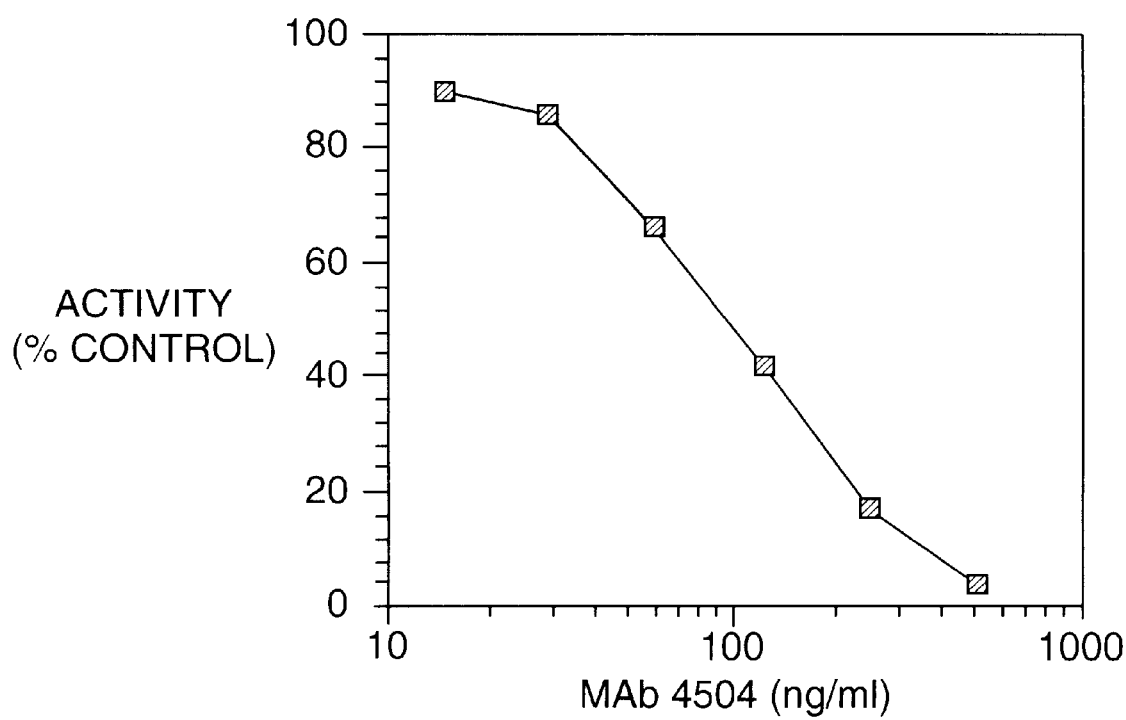
FIG. 12 Characterisation of the coagulant activity on ECV-304 cells in the microcarrier assay by the use of a neutralising monoclonal antibody to human TF (American Diagnostica cat#4504). Almost all clotting activity can be abolished by the neutralising antibody, thus demonstrating that it is highly dependent on the function of TF.

The system obtained can be shown to faithfully represent the extrinsic pathway of coagulation, by the use of a panel of immunodepleted human plasmas deficient in each of the coagulation factors. Coagulation mediated by e.g. ECV304 human endothelial cells (American Culture Collection CRL-1998) is clearly dependent on FVII and FX (FIG. 11). Thus there is no direct activation of FX; the coagulation is mediated by cell-surface TF/FVIl. That this procoagulant activity really represents TF-mediated coagulation was demonstrated by the use of a neutralising monoclonal antibody to human TF, which could abolish all coagulation activity (FIG. 12).

EXAMPLE 11
Inhibition of TF/FVII Assay by FVII Peptides
ELISA Assay

Figure 13:
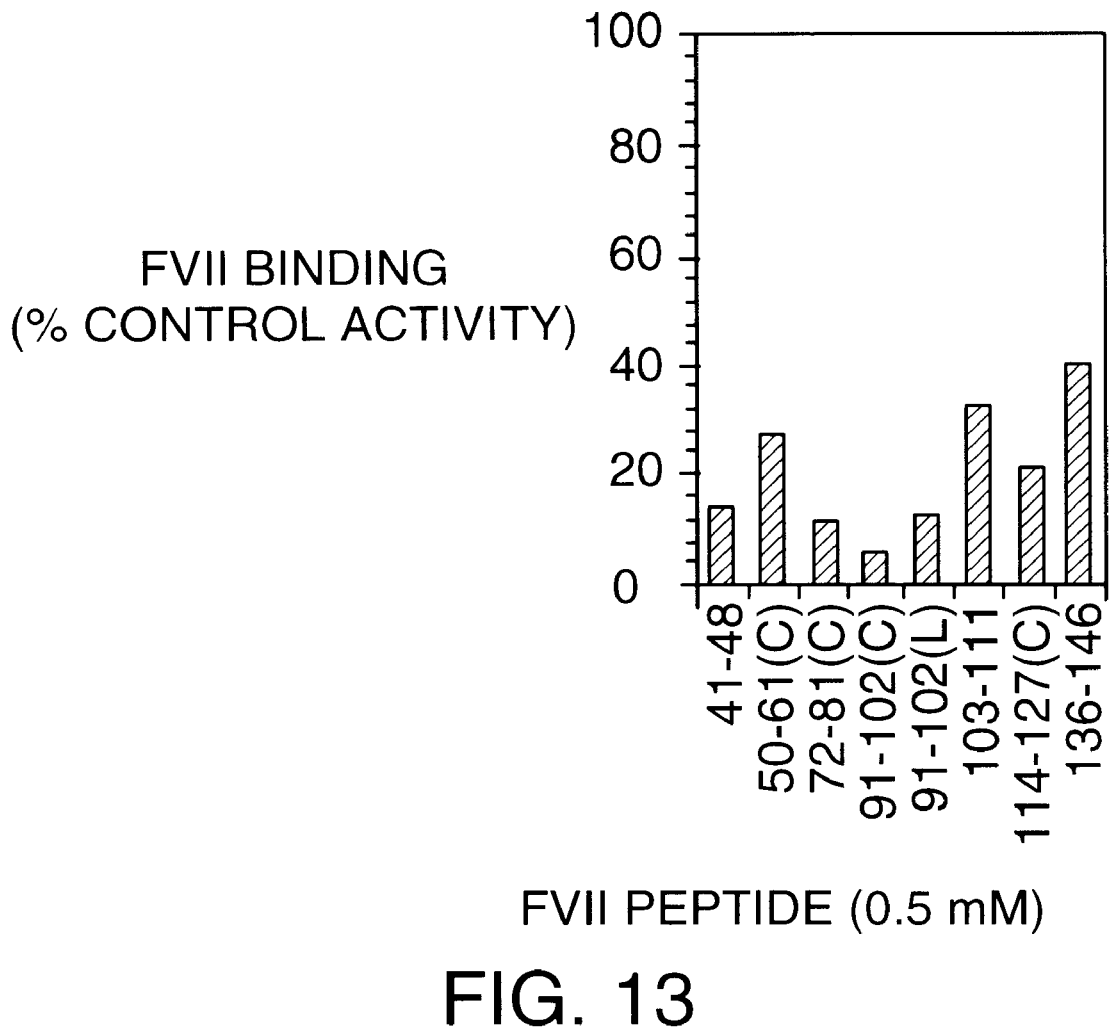
FIG. 13 ELISA assay of the inhibition of FVII binding to immobilized rTF produced by synthetic FVII peptides (all at 0.5 mM). For peptide sequences see the table of peptides below (page 19). C and L denote the cyclic and linear forms respectively of peptides with terminal cysteines.

The inhibition results shown in FIG. 13 indicate that in addition to sequences from the "hinge" region (i.e. residues 41–48 between the GLA domain and the first EGF domain, UNIVERSITY OF TEXAS) and from the first EGF domain itself (i.e. residues 50–61; Clarke et al), there exist additional sequences in the second EGF domain (especially 95–104) which are inhibitors when presented as peptides in this binding assay.

The results of the above peptide inhibition experiments are tabulated below:

Summary of Peptide Inhibition Results

| FVII peptide $IC_{50}$ (mM) or % inhibition at 0.5 mM[a] | | | |
|---|---|---|---|
| Sequence[b] | | | |
| Amidolytic apo TF Assay | Amidolytic Microcarrier assay | ELISA binding assay | Coagulation microcarrier assay |
| 72–81(C) | 2.40 | 0.35 | 89% | (22%) |
| 91–102(C) | 0.60 | | 0.04 | 0.58 |
| 91–102(L) | 1.14 | | 0.06 | (14%) |
| 91–102(anal)[c] | 1.30 | | 0.05 | 1.50 |
| 103–111 | 2.20 | 0.87 | 59% | (30%) |
| 114–127(C) | (21%) | | (77%) | (44%) |

[a]Percent inhibition at 0.5 mM is given for those peptides which did not reach quantitative or near-quantitative inhibition at the highest test concentration (1 mM).
[b]The sequence numbers given are with reference to the native sequence of human FVII. C and L refer to the disulfide cyclised and linear forms respectively.
[c]91–102(anal) has an arginine residue at position 100, in place of glutamine.

EXAMPLE 12
Validation of Specificity of Peptide Inhibitors

The effect of the peptides observed in the coagulation assay could conceivably have been due to effects on another one or more of the several components contributing to the coagulation cascade. This possibility was therefore tested by adding the peptides to coagulation assays which were initiated by contact activation (Cephotest™, Nycomed), and therefore involved coagulation factors of the intrinsic and common pathways of coagulation, i.e. all coagulation factors other than TF/FVII. The peptides 95–104, 91–102 and 103–111 were inactive in this system, while control inhibitors of FX (TAP) and thrombin (Hirudin; HIR) were strongly inhibitory. Thus evidence was obtained that the effects observed in the TF/FVII initiated coagulation assay above were in fact due to a direct effect on the TF/FVII complex.

We claim:

1. A peptide having an amino acid sequence consisting of;

| CVNENGGCEQYCSD | (SEQ ID NO: 4), | IA |
| FCLPAFEGRNCE | (SEQ ID NO: 5), | IB |
| RCHEGYSLLADGVSCT | (SEQ ID NO: 6), | IC | or esters, amides, salts or cyclic derivatives thereof or functional analogues or fragments thereof having substantially similar activity to peptides IA, IB and IC, wherein said fragments have at least five amino acids and exclude the peptides

| CVNEGGCEQYC | (SEQ ID NO: 7) | IIA |
| CLPAFEGRNC | (SEQ ID NO: 8) | IIB |
| and | | |
| CHEGYSLLADGVSC | (SEQ ID NO: 9). | IIC |

2. The peptides of claim 1 which are cyclic.

3. A method for preventing formation of a functional tissue factor/FVIIa complex comprising applying a pharmaceutical composition comprising peptides having an amino acid sequence consisting of:

| CVNENGGCEQYCSD | (SEQ ID NO: 4), | IA |
| FCLPAFEGRNCE | (SEQ ID NO: 5), | IB |
| RCHEGYSLLADGVSCT | (SEQ ID NO: 6), | IC | or esters, amides, salts or cyclic derivatives thereof, or analogues or fragments thereof, said esters, amides, salts, cyclic derivatives, analogues or fragments having substantially similar ability to prevent formation of functional tissue factor/FVIIIa complex as peptides IA, IB or IC.

4. The method of claim 3 wherein the peptides of formula IA, IB and IC are fragments having at least 5 amino acids.

5. Pharmaceutical compositions comprising one or more peptides having an amino acid sequence consisting of formula IA, IB or IC of claim 2, or analogues, fragments or salts thereof having substantially similar ability to prevent formation of functional tissue factor/FVIIIa complex as peptides IA, IB or IC, together with a physiologically acceptable excipient, said fragments having at least five amino acids.

6. A method of treating blood disorders in a mammal, said method comprising administering to said mammal an effective amount of one or more peptides having an amino acid sequence consisting of formula IA, IB or IC of claim 2, or analogues, fragments or salts thereof, having substantially similar ability to prevent formation of functional tissue factor/FVIIIa complex as peptides IA, IB or IC.

7. A process for the preparation of peptides having an amino acid sequence consisting of formula IA, IB or IC of claim 2, said process comprising the step of deprotecting a protected derivative of a peptide of formula IA, MB or IC.

8. A peptide selected from the group consisting of:

| CVNENGGCEQYCSD | (SEQ ID NO: 4) | IA, |
| FCLPAFEGRNCE | (SEQ ID NO: 5) | IB, |
| and | | |
| RCHEGYSLLADGVSCT | (SEQ ID NO: 6). | IC |

9. A peptide selected from the group consisting of: VNENG (SEQ ID NO: 10), ENGGC (SEQ ID NO: 12), GGCEQ (SEQ ID NO: 14), CEQYV (SEQ ID NO: 15), NGGCEQYCSD (SEQ ID NO: 11) and GGCEQYCSD (SEQ ID NO: 13).

10. A peptide selected from the group consisting of: ENGGA (SEQ ID NO: 16), GGAEQ (SEQ ID NO: 17) and AEQYV (SEQ ID NO: 18).

11. A peptide having an amino acid sequence consisting of EQYVNE (SEQ ID NO: 19).

12. The method of claim 4 wherein the fragments are selected from the group consisting of: VNENG (SEQ ID NO: 10), ENGGC (SEQ ID NO: 12), GGCEQ (SEQ ID NO: 14), CEQYV (SEQ ID NO: 15), NGGCEQYCSD (SEQ ID NO: 11) and GGCEQYCSD (SEQ ID NO: 13).

13. The method of claim 4 wherein the fragments are selected from the group consisting of: ENGGA (SEQ ID NO: 16), GGAEQ (SEQ ID NO: 17) and AEQYV (SEQ ID NO: 18).

14. The method of claim 4 wherein the fragment has the sequence EQYVNE (SEQ ID NO: 19).

15. The method of claim 4 wherein the peptides are cyclic.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:

(A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:1:

Val Gly His Phe Gly Val
1               5

(2) INFORMATION FOR SEQ ID NO:2:

(i) SEQUENCE CHARACTERISTICS:
            (A) LENGTH: 11 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:2:

Ser Asp His Thr Gly Thr Lys Arg Ser Cys Arg
1               5                   10

(2) INFORMATION FOR SEQ ID NO:3:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:3:

Ser Asp His Thr Gly Thr Lys Arg Ser Cys
1               5                   10

(2) INFORMATION FOR SEQ ID NO:4:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:4:

Cys Val Asn Glu Asn Gly Gly Cys Glu Gln Tyr Cys Ser Asp
1               5                   10

(2) INFORMATION FOR SEQ ID NO:5:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Phe Cys Leu Pro Ala Phe Glu Gly Arg Asn Cys Glu
1               5                   10

(2) INFORMATION FOR SEQ ID NO:6:

(i) SEQUENCE CHARACTERISTICS:

(A) LENGTH: 16 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Arg Cys His Glu Gly Tyr Ser Leu Leu Ala Asp Gly Val Ser Cys Thr
1               5                  10                  15

(2) INFORMATION FOR SEQ ID NO:7:

(i) SEQUENCE CHARACTERISTICS:
            (A) LENGTH: 12 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Cys Val Asn Glu Asn Gly Gly Cys Glu Gln Tyr Cys
1               5                  10

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Cys Leu Pro Ala Phe Glu Gly Arg Asn Cys
1               5                  10

(2) INFORMATION FOR SEQ ID NO:9:

(i) SEQUENCE CHARACTERISTICS:
            (A) LENGTH: 14 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Cys His Glu Gly Tyr Ser Leu Leu Ala Asp Gly Val Ser Cys
1               5                  10

(2) INFORMATION FOR SEQ ID NO:10:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Val Asn Glu Asn Gly
1               5

(2) INFORMATION FOR SEQ ID NO:11:

(i) SEQUENCE CHARACTERISTICS:

(A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:11:

Asn Gly Gly Cys Glu Gln Tyr Cys Ser Asp
1               5                   10

(2) INFORMATION FOR SEQ ID NO:12:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Glu Asn Gly Gly Cys
1               5

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Gly Gly Cys Glu Gln Tyr Cys Ser Asp
1               5

(2) INFORMATION FOR SEQ ID NO:14:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:14:

Gly Gly Cys Glu Gln
1               5

(2) INFORMATION FOR SEQ ID NO:15:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:15:

Cys Glu Gln Tyr Val
1               5

(2) INFORMATION FOR SEQ ID NO:16:

(i) SEQUENCE CHARACTERISTICS:

(A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:16:

Glu Asn Gly Gly Ala
1               5

(2) INFORMATION FOR SEQ ID NO:17:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:17:

Gly Gly Ala Glu Gln
1               5

(2) INFORMATION FOR SEQ ID NO:18:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:18:

Ala Glu Gln Tyr Val
1               5

(2) INFORMATION FOR SEQ ID NO:19:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:19:

Glu Gln Tyr Val Asn Glu
1               5

(2) INFORMATION FOR SEQ ID NO:20:

(i) SEQUENCE CHARACTERISTICS:
          (A) LENGTH: 8 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:20:

Leu Phe Trp Ile Ser Tyr Ser Asp
1               5

(2) INFORMATION FOR SEQ ID NO:21:

(i) SEQUENCE CHARACTERISTICS:

(A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:21:

Trp Ile Ser Tyr Ser Asp Gly Asp
1               5

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:22:

Ser Tyr Ser Asp Gly Asp
1               5

(2) INFORMATION FOR SEQ ID NO:23:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:23:

Cys Ala Ser Ser Pro Cys Gln Asn Gly Gly Ser Cys
1               5                   10

(2) INFORMATION FOR SEQ ID NO:24:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Lys Asp Gln Leu Gln Ser Tyr Ile
1               5

(2) INFORMATION FOR SEQ ID NO:25:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Ser Asp His Thr Gly Thr Lys Arg Ser
1               5

(2) INFORMATION FOR SEQ ID NO:26:

(i) SEQUENCE CHARACTERISTICS:

(A) LENGTH: 11 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:26:

```
Gly Lys Ile Pro Ile Leu Glu Lys Arg Asn Ala
1               5                   10
```